United States Patent [19]

Prada-Silva et al.

[11] Patent Number: 4,775,696

[45] Date of Patent: Oct. 4, 1988

[54] SYNTHESIS GAS TO ALCOHOLS PROCESS

[75] Inventors: Guillermo Prada-Silva; Jitendra A. Patel, both of Wappingers Falls; Ajit K. Bhattacharya, Hopewell Junction, all of N.Y.

[73] Assignee: Texaco Inc., White Plains, N.Y.

[21] Appl. No.: 945,264

[22] Filed: Dec. 22, 1986

[51] Int. Cl.$^4$ .............................................. C07C 27/06
[52] U.S. Cl. ................................... 518/714; 518/717; 518/721; 502/200; 518/728
[58] Field of Search ................ 518/714, 728, 717, 721

[56] References Cited

U.S. PATENT DOCUMENTS 4,661,525  4/1987  Grazioso et al. .................... 518/714
4,675,344  6/1987  Conway et al. ..................... 518/714

Primary Examiner—Howard T. Mars
Attorney, Agent, or Firm—Robert A. Kulason; James J. O'Loughlin

[57] ABSTRACT

A method for preparing a mixture of lower aliphatic alcohols from the reaction of carbon monoxide and hydrogen in the presence of a sulfide-containing heavy metal catalyst under carbon monoxide-hydrogenation conditions in which said catalyst comprises at least one sulfided heavy metal element selected from the group consisting of molybdenum, tungsten, rhenium, and an alkali or alkaline earth promoter which has been treated with a nitrogen-containing compound, or a thermally stable derivative thereof is provided.

8 Claims, No Drawings

SYNTHESIS GAS TO ALCOHOLS PROCESS

BACKGROUND OF THE INVENTION

Field of the Invention

This invention broadly relates to a process for preparing aliphatic alcohols from synthesis gas and more particularly to an improved process in which a sulfided heavy metal catalyst is employed to effect the hydrogenation of carbon monoxide to produce a mixture of lower aliphatic alcohols.

Lower aliphatic alcohols have been proposed as octane enhancers or as a replacement for gasoline in fueling internal combustion engines. Certain mixtures of lower aliphatic alcohols have the EPA approval for use and are currently being marketed in the United States. The lower aliphatic alcohols can be produced from domestically available non-petroleum sources and the use of these alcohols in fuel compositions can serve to lessen the nation's dependence on foreign sources of crude oil and petroleum products.

Hydrogen and carbon monoxide, or synthesis gas, a mixture of hydrogen and carbon monoxide, can be reacted to form a mixture of lower aliphatic alcohols. The synthesis gas feedstream can be produced from such non-petroleum sources as coal and biomass in well known partial oxidation reactions.

Numerous catalytic processes have been studied in attempts to provide a viable process for the production of aliphatic alcohols from synthesis gas. The early efforts were primarily directed to the production of methanol. More recently, attention has been directed to the production of higher aliphatic alcohols or a mixture of higher aliphatic alcohols with methanol. Such a mixture is highly suitable as an octane enhancing component for motor fuel and as a substitute for tetraalkyl lead additives in motor fuel.

A number of proposed processes have suggested the use of alkali promoted sulfided heavy metal catalysts for producing aliphatic alcohols from synthesis gas. These processes have an advantage in that sulfided heavy metal catalysts are more stable in the presence of minor amounts of sulfur compounds commonly found in the synthesis gas feed. However, the alcohol selectivity of sulfided heavy metal catalysts is adversely effected at higher reaction temperatures in the alcohol process.

DISCLOSURE STATEMENT

U.S. Pat. Nos. 4,243,553 and 4,243,554 discloses a molybdenum disulfide catalyst that is useful in the water gas shift, methanation, hydrogenation and dehydrogenation processes. U.S. Pat. Nos. 4,607,056 and 4,607,055 disclose synthesis gas to alcohol processes in which the catalyst comprises molybdenum in combination with a metal from the group consisting of cobalt, iron and nickel in an oxide form with an alkali metal promoter.

EPA No. 0 119609 discloses an alkali promoted molybdenum disulfide catalyst that is useful for producing aliphatic alcohols from synthesis gas. The disclosures in U.S. Pat. Nos. 4,243,553, 4,243,554, 4,607,056, 4,607,055 and EPA No. 0119609 are incorporated herein by reference.

SUMMARY OF THE INVENTION

It has been discovered that a mixture of carbon monoxide and hydrogen can be reacted in the presence of a treated sulfided heavy metal catalyst to form a mixture of lower aliphatic alcohols. More specifically, an improved process has been discovered which employs a catalyst comprising (1) at least one sulfided heavy metal element from the group consisting of molybdenum, tungsten and rhenium, (2) optionally, a sulfided heavy metal element from the group consisting of cobalt, iron and nickel.

(3) a nitrogen-containing compound, or a thermally stable derivative thereof, (4) a promoter comprising an alkali or alkaline earth element in free or combined form, and, optionally (5) a support, This invention also encompasses a method for improving the thermal stability and effectiveness of a sulfided heavy metal catalyst for converting synthesis gas to alcohols wherein said catalyst is treated with a nitrogen-containing compound, or a thermally stable derivative thereof.

DETAILED DESCRIPTION OF THE INVENTION

In accordance with this invention, synthesis gas or a mixture of carbon monoxide and hydrogen is reacted under carbon monoxide hydrogenation conditions in the presence of a catalyst comprising:

(1) at least one sulfided heavy metal element selected from the group consisting of molybdenum, tungsten and rhenium, (2) optionally, a sulfided heavy metal element from the group consisting of cobalt, iron and nickel (3) a nitrogen-containing compound, or a thermally stable derivative thereof, (4) a promoter comprising an alkali or alkaline earth element in free or combined form, and optionally (5) a support.

The method for treating a sulfide-containing heavy metal catalyst comprises forming (1) at least one sulfided heavy metal element from the group consisting of molybdenum, tungsten and rhenium, (2) optionally forming a sulfided heavy metal element from the group consisting of cobalt, iron and nickel, (3) treating said sulfided heavy metal element or elements with a nitrogen-containing compound or a thermally stable derivative thereof, and (4) combining an alkali or an alkaline earth metal element in free or combined form with said treated sulfided heavy metal element.

In a more specific aspect of the invention, sulfided molybdenum, such as molybdenum disulfide, or a mixture of sulfided heavy metals, such as sulfided molybdenum and cobalt, either in bulk or on a support, is treated with a nitrogen-containing base, such as melamine or a thermally stable derivative thereof such as melem or melon.

Synthesis gas or a mixture of hydrogen and carbon monoxide employed in this process can be obtained by methods well known in the art. The two gas components can be provided separately and combined for the reaction or the two components can be generated simultaneously in a synthesis gas process, such as a coal gasification process. The feed gas to the alcohol process may employ the hydrogen to carbon monoxide in amounts broadly ranging from about 1 to 20 moles of hydrogen per mole of carbon monoxide. The preferred mole ratio for alcohol production is from about 1 to 5 moles of hydrogen per mole of carbon monoxide.

Sulfided heavy metal catalysts suitable for the synthesis gas to alcohols process can be prepared in a number of ways. The catalyst composition may be prepared in bulk, that is, without a catalyst support or carrier. It is also common to prepare catalyst compositions using a support for the active metal components. When such a catalyst support or carrier is employed it may comprise a relatively refractory, porous, absorptive high surface area material. Conventional catalyst supports comprise materials such as alumina, silica, titania, magnesia, silica-alumina and boron phosphates. Catalysts comprising the noted support materials are disclosed in U.S. Pat. No. 4,098,683 and this patent is incorporated herein by reference.

A proposed method for preparing a sulfided heavy metal catalyst is by chemically precipitating a heavy metal component from an aqueous solution of a soluble heavy metal compound. One or more soluble salts of the prescribed heavy metals may be employed. The heavy metal components may be precipitated simultaneously or in sequence. In general practice, the heavy metal compound is precipitated by the addition of a base to an aqueous solution of the heavy metal compound. In a catalyst preparation process which is specifically concerned with making a sulfided heavy metal catalyst, it is convenient to use an aqueous ammonium sulfide solution to effect the precipitation of the heavy metal compounds in a sulfided form. To promote complete formation of a sulfided precipitate, the mixture is stirred for a substantial period of time at a moderately elevated temperature. It has been found that stirring for several hours while maintaining the mixture at a temperature ranging from 50° to 60° C. is highly effective. Subsequent to precipitation, the solution is filtered and the precipitate is dried under vacuum. Decomposition of the precipitated heavy metal compound to form the final sulfided heavy metal state is preferably carried out by heating the precipitate at an elevated temperature under an inert atmosphere. In general, the precipitate is heated to a temperature ranging from about 300° to 700° C. Nitrogen is preferred as the inert atmosphere and it is advantageous to have a stream of nitrogen flowing through the precipitate during the calcination step.

An alkaline-reacting promoter is essential in order to provide a catalyst which is effective in the synthesis gas to alcohol process. Broadly, the promoter may comprise an alkali or an alkaline earth metal element in free or combined form. The alkali metals are the preferred promoters with potassium, cesium and rubidium being particularly preferred.

A nitrogen-containing sulfided heavy metal catalyst may be prepared by treating the heavy metal components with appropriate sulfur and nitrogen-containing compounds. The sulfur compound may be selected from the group consisting of hydrogen sulfide, ammonium sulfide, alkali or alkaline earth metal sulfides. A wide variety of nitrogen compounds may be employed in the catalyst preparation. The nitrogen compound may be selected from the group consisting of urea, dimethylolurea, cyanuric acid, melamine, melam, melem, or melon. A compound containing both nitrogen and sulfur such as thiourea and trithiocyanuric acid may also be employed. Ammonium sulfide and melamine are preferred sulfur and nitrogen-containing starting materials.

According to the present invention a nitrogen-containing starting material may be a monomer or a dimeric, trimeric or polymeric condensation product. Structural features such as s-triazine (I) and tri-s-triazine (II) are preferred. For example:

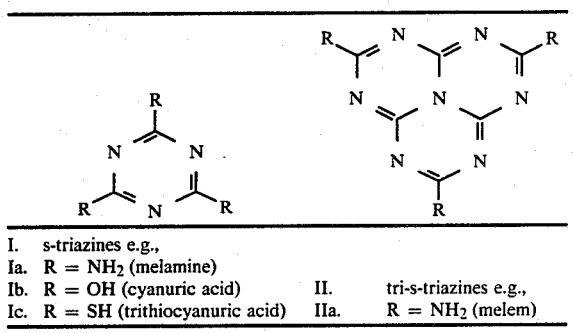

I. s-triazines e.g.,
Ia. R = NH$_2$ (melamine)
Ib. R = OH (cyanuric acid)   II. tri-s-triazines e.g.,
Ic. R = SH (trithiocyanuric acid)   IIa. R = NH$_2$ (melem)

The chemistry of "s-triazines and derivatives" has been presented in great detail in the "The Chemistry of Heterocyclic Compounds", Vol. 13, E. M. Smolin and L. Rapoport, Interscience Publishers Inc. (1967) and is incorporated herein by reference.

When heated above its melting point in the absence of ammonia, melamine (mp 354° C.) decomposes with loss of ammonia to afford melam (III), melem (IIa), and melon.

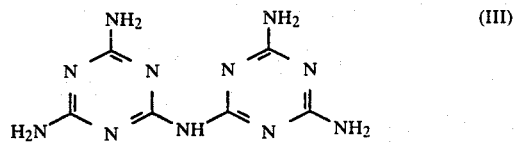

"In melamine deammonation, melam is formed first by loss of an equivalent of ammonia from two molecules of melamine. Melem is usually found together with melam and is possibly the end product of rearrangement of melam (III).

Heating the reaction mixture at 600° C. causes further loss of ammonia with the formation of melon, a compound, or rather substance, which can survive red heat."

For the novel process of the invention, the sulfided heavy metal catalyst is treated with a nitrogen-containing compound at an intermediate point in the preparation of the catalyst. The precipitated sulfide heavy metal component of the catalyst is filtered and separated from the mother liquor. This precipitate is treated with an aqueous solution of a nitrogen-containing compound, preferably a base such as melamine. Treating is effected using a relatively dilute, aqueous solution of the nitrogen-containing compound. In general, the aqueous preparation may contain from about 0.1 to 20 weight percent of the nitrogen-containing compound with a concentration from about 0.5 to 10 weight percent being preferred. The aqueous treatment may be further improved by incorporating a soluble sulfide compound therein. Ammonium sulfide is particularly preferred as a component of the mixture containing the nitrogen-containing compound. The sulfide compound may be employed in an amount ranging from about 0.1 to 20 weight percent.

The mixture of the sulfided heavy metal catalyst and the aqueous nitrogen-containing compound are thoroughly mixed to incorporate the nitrogen-containing compound onto the sulfided heavy metal catalyst. Continuous stirring while the mixture is maintained at a moderately elevated temperature from about 50° to 60° C. for an hour or for several hours has been found effective. The treated sulfided heavy metal catalyst is then separated from the mixture by filtration and dried under a vacuum. The treated sulfided heavy metal catalyst is subjected to calcination. In general, calcination is effected at an elevated temperature ranging from about 300° to 700° C. while under an inert atmosphere. A preferred calcination temperature range is from about 400° to 600° C. It is preferred to conduct the calcination while passing a stream of inert gas, such as nitrogen, over the catalyst.

Following calcination, the catalyst is combined with the prescribed promoter, namely an alkali metal or an alkali earth metal element. The promoter can be combined with the heavy metal component in a variety of ways. A preferred method is to physically mix the promoter with the heavy metal components in a blending mill or other type of mixing equipment.

The final catalyst composition for the process of the invention may contain an amount of the thermally stable nitrogen-containing compound that will provide from about 0.01 to 20 weight percent of nitrogen, calculated as $N_2$, based on the total weight of the catalyst. A preferred concentration of this component is from about 0.05 to 10.0 weight percent.

The composition of the finished catalyst can be expressed in terms of its relative elemental composition. Broadly expressed the catalyst may have a relative elemental composition from the presented element as follows:

Heavy metal $(s)_{1-10}$ Alkali component$_{0.1-10.0}$
Sulfur$_{1-20}$ Nitrogen$_{0.01-10}$.

A specific catalyst may have the following relative elemental composition:

$K_{0.5-1.2} Co_{1-2} Mo_{0.5-1.5} S_{3.5-5} N_{0.05-0.15}$

The following Examples illustrate applicants' novel process based on the use of a sulfided heavy metal catalyst which has been treated with a nitrogen-containing compound.

EXAMPLE I (COMPARISON EXAMPLE)

An ammonium molybdate solution is prepared by dissolving 73 grams of molybdenum oxide in 494 millileters of aqueous ammonia containing 17% $NH_3$. An aqueous cobalt nitrate solution is prepared by dissolving 74 grams of this salt in 90 millileters of water. An ammonium solution containing both cobalt and molybdenum is obtained by slowly mixing the two solutions. 1000 millileters of aqueous ammonium sulfide containing 22% $(NH_4)_2S$ is mixed with the ammoniacal solution of the heavy metal salts producing a co-precipitate of ammonium tetrathiomolybdate and cobalt sulfide. The mixed solution is stirred while maintaining it at 50° to 60° C. for about 2 hours. The precipitate is then filtered and dried under a vacuum at about 15° C.

Subsequently, the dried precipitate is subjected to calcination. The calcination is carried out at about 450° C. while nitrogen is passed over the heavy metal catalyst component at a rate of 25 millileters of nitrogen per minute. During calcination, the tetrathiomolybdate formed during precipitation from the aqueous solution of the heavy metal salts is decomposed to molybdenum disulfide. The cooled heavy metal sulfides are then physically mixed with potassium carbonate to incorporate potassium into the catalyst.

A typical elemental composition for a catalyst prepared as above identified as catalyst S-13 is as follows:

$K_{0.5} Co_{0.7} Mo_{1.0} S_{2.9}$

EXAMPLE II

An ammonium molybdate solution is prepared by dissolving 73 grams of molybdenum oxide in 494 millileters of aqueous ammonia containing 17% $NH_3$. An aqueous cobalt nitrate solution is prepared by dissolving 74 grams of this salt in 90 millileters of water. An ammonium solution containing both cobalt and molybdenum is obtained by slowly mixing the two solutions. 1000 millileters of an aqueous ammonium sulfide solution containing 22% $(NH_4)_2S$ is added to the solution of the heavy metal salts and a co-precipitate of ammonium tetrathiomolybdate and cobalt sulfide is obtained. The mixed solution is stirred at 50° to 60° C. for 2 hours followed by filtration of the co-precipitate.

The co-precipitate is added to an aqueous solution containing 1% melamine and 2% ammonium sulfide. This mixture is stirred at 50° to 60° C. for about 2 hours followed by filtration and drying under vacuum at about 50° C. Calcination and decomposition of the co-precipitate is carried out by heating to about 45° C. under a nitrogen stream at a flow rate of about 25 millileters per minute. The co-precipitate is cooled and mixed with potassium carbonate. Mixing is effected physically via the use of a fine mill. Relative elemental composition of this catalyst identified as Catalyst S-16 is as follows:

$K_{0.8} Co_{1.5} Mo_{1.0} S_{4.4} N_{0.1}$

The effectiveness of the catalysts for converting a mixture of carbon monoxide and hydrogen in a mixture of lower aliphatic alcohols was tested in a fixed bed reactor. About 20 cc of catalyst were placed in a fixed bed reactor. The reaction conditions were 1500 psig, $H_2$: CO ratio of 2:1 and gas hourly space velocity of 10,000 hr.$^{-1}$. The selectivity, productivity and conversions were determined at increasing reaction temperatures. The results are set forth in Table I below.

TABLE 1

COMPARISON OF CATALYST PERFORMANCE S-13 vs S-16
Run Conditions: P = 1500 psig, GHSV = 10,000 hr$^{-1}$, $H_2$:CO = 2:1

| | Temperature, °C. | | | | | |
|---|---|---|---|---|---|---|
| | 320 | | 330 | | 343 | |
| Catalyst | S-13 | S-16 | S-13 | S-16 | S-13 | S-16 |
| Alc. Selectivity (CO$_2$ Free Basis) | 80.1 | 82.1 | 78.7 | 84.3 | 69.7 | 80.3 |
| Alc. Productivity g/g-hr | 0.27 | 0.24 | 0.34 | 0.30 | 0.34 | 0.42 |
| CO Conversion, % | 15.6 | 7.0 | 21.8 | 11.5 | 28.6 | 18.3 |
| C$_2$OH/C$_1$OH | 0.36 | 0.29 | 0.45 | 0.39 | 0.53 | 0.49 |
| Liquid Composition, wt % | | | | | | |
| Methanol | 70.2 | 75.4 | 65.1 | 68.8 | 61.7 | 63.6 |
| Ethanol | 21.3 | 20.3 | 22.8 | 22.7 | 21.9 | 25.4 |
| C$_{3-6}$ Alc. | 4.4 | 1.7 | 6.7 | 4.7 | 11.1 | 6.0 |
| Oxygenates | 0.4 | 0.5 | 0.6 | 0.5 | 0.6 | 0.4 |
| Water | 2.0 | 1.2 | 2.4 | 1.4 | 3.3 | 1.6 |

The foregoing data shows that the nitrogen-compound treated sulfided heavy metal catalyst provided a substantially improved selectivity to alcohols at higher reaction temperatures.

We claim:

1. In a method of preparing a mixture of lower aliphatic alcohols which comprises reacting carbon monoxide and hydrogen in the presence of a sulfide-containing heavy metal catalyst under cabon monoxide-hydrogenation conditions, said catalyst comprising:
   (1) at least one sulfided heavy metal element selected from the group consisting of molybdenum; tungsten, and rhenium,
   (2) a sulfided heavy metal element form the group consisting of cobalt, iron, and nickel,
   (3) a promoter comprising an alkali or alkaline earth element in free or combined form, and optionally,
   (4) a support, the improvement which comprises improving the selectivity to said alcohols by treating said sulfided heavy metal elements with a mitrogen-containing base prior to treatment with said promoter, said nitrogen-containing base being selected from the group consisting of urea, dimethylolurea, cyanuric acid, melamine, melam, melem, and melon.

2. A method according to claim 1 in which said nitrogen-containing base is malamine.

3. A method according to claim 1 in which said nitrogen-containing compound is melam.

4. A method according to claim 1 in which said nitrogen-containing base is melem.

5. A method according to claim 1 in which said nitrogen-containing compound is melon.

6. A method according to claim 1 in which said catalyst contains from about 0.01 to 10 weight percent nitrogen.

7. A method according to claim 3 in which said catalyst contains from about 0.01 to 10 weight percent of nitrogen, calculated as $N_2$ from said nitrogen-containing compound.

8. A method according to claim 1 in which said catalyst has the following elemental composition:

$$K_{0.5-1.2}\ Co_{1-2}\ Mo_{0.5-1.5}\ S_{3.5-5}\ N_{0.05-0.15}.$$

* * * * *